United States Patent
Kim et al.

(10) Patent No.: US 12,008,748 B2
(45) Date of Patent: Jun. 11, 2024

(54) METHOD FOR CLASSIFYING FUNDUS IMAGE OF SUBJECT AND DEVICE USING SAME

(71) Applicant: VUNO, INC., Seoul (KR)

(72) Inventors: Sang Keun Kim, Seoul (KR); Hyun-Jun Kim, Gyeonggi-do (KR); Kyuhwan Jung, Seoul (KR); Jae Min Son, Gyeonggi-do (KR)

(73) Assignee: VUNO, INC., Seoul (KR)

( * ) Notice: Subject to any disclaimer, the term of this patent is extended or adjusted under 35 U.S.C. 154(b) by 791 days.

(21) Appl. No.: 17/059,868

(22) PCT Filed: Apr. 10, 2019

(86) PCT No.: PCT/KR2019/004288
§ 371 (c)(1),
(2) Date: Nov. 30, 2020

(87) PCT Pub. No.: WO2019/231102
PCT Pub. Date: Dec. 5, 2019

(65) Prior Publication Data
US 2021/0219839 A1 Jul. 22, 2021

(30) Foreign Application Priority Data
May 31, 2018 (KR) .................. 10-2018-0062475

(51) Int. Cl.
*G06T 7/00* (2017.01)
*G06T 7/187* (2017.01)
*G16H 30/20* (2018.01)

(52) U.S. Cl.
CPC ............ *G06T 7/0012* (2013.01); *G06T 7/187* (2017.01); *G16H 30/20* (2018.01); *G06T 2207/30041* (2013.01)

(58) Field of Classification Search
CPC ............ G06T 7/0012; G06T 7/187; G06T 2207/30041; G16H 30/20
See application file for complete search history.

(56) References Cited

U.S. PATENT DOCUMENTS

| | | | |
|---|---|---|---|
| 2010/0220906 A1* | 9/2010 | Abramoff | G06F 18/2415 382/165 |
| 2018/0235467 A1* | 8/2018 | Celenk | A61B 3/14 |
| 2020/0288972 A1* | 9/2020 | Park | A61B 3/14 |
| 2021/0042912 A1* | 2/2021 | Zhao | G06V 10/82 |
| 2021/0224977 A1* | 7/2021 | Jia | G06F 18/24 |

FOREIGN PATENT DOCUMENTS

| | | |
|---|---|---|
| KR | 10-2013-0000576 | 1/2013 |
| KR | 10-2014-0108417 | 9/2014 |
| KR | 10-2015-0094080 | 8/2015 |
| KR | 10-1848321 | 4/2018 |
| KR | 10-1848322 | 4/2018 |
| KR | 10-2018-0057420 | 5/2018 |

* cited by examiner

*Primary Examiner* — Khai M Nguyen
(74) *Attorney, Agent, or Firm* — IP & T GROUP LLP (57) ABSTRACT

The present invention relates to a method for classifying a fundus image and a device using same. Specifically, according to the method of the present invention, a computing device acquires a fundus image of a subject, generates classification information of the fundus image, generates an interpretation text on the basis of the classification information, and provides the interpretation text to an external entity.

17 Claims, 8 Drawing Sheets

| Retinal Specialist | Glaucoma Specialist | Optic Nerve Specialist |
|---|---|---|
| [Number of references/ Number of possible references] | [Number of references/ Number of possible references] | [Number of references/ Number of possible references] |
| CHOI, Bae-Dal [Assistant professor in university A]: 212/500<br>BANG, Jung-Hwan [Specialist in university B]: 13/300<br>HONG, Gild-Dong [Fellow in university C]: 212/400<br>⋮ ⋮ ⋮ ⋮ ⋮ ⋮ ⋮ ⋮ | KIM, Chi-Gook [Assistant professor in university A]: 212/500<br>JUNG, Sang-In [Specialist in university B]: 13/300<br>PARK, Cheol-Soo [Fellow in university C]: 212/400<br>⋮ ⋮ ⋮ ⋮ ⋮ ⋮ ⋮ ⋮ | SON, Jae-Min [Chair professor in university D]: 212/500<br>LEE, Young-Nam [Resident in university E]: 13/300<br>HWANG, Dang-Hae [Fellow in university F]: 212/400<br>⋮ ⋮ ⋮ ⋮ ⋮ ⋮ ⋮ ⋮ |

Click and refer

| Findings | AUROC | | Sen | | Spe | | AIR (TP) | | AIR (FN) | |
|---|---|---|---|---|---|---|---|---|---|---|
| | With | Without | With | Without | With | Without | With | Without | With | Without |
| Macular hole | 0.9867 | 0.9676 | 0.9726 | 0.8904 | 0.9686 | 0.9781 | 0.9999 | 0.3156 | 0.9999 | 0.2611 |
| Hard exudate | 0.9900 | 0.9910 | 0.9521 | 0.9656 | 0.9604 | 0.9412 | 0.8089 | 0.5999 | 0.5750 | 0.4614 |
| Hemorrhage | 0.9876 | 0.9895 | 0.9405 | 0.9381 | 0.9607 | 0.9662 | 0.8890 | 0.6388 | 0.4899 | 0.3857 |
| Membrane | 0.9805 | 0.9795 | 0.9533 | 0.9305 | 0.9181 | 0.9451 | 0.9699 | 0.3696 | 0.8446 | 0.2499 |
| Drusen | 0.9808 | 0.9786 | 0.9448 | 0.9292 | 0.9192 | 0.9261 | 0.8292 | 0.5611 | 0.5931 | 0.4012 |
| Cotton wool patch | 0.9725 | 0.9741 | 0.9100 | 0.9336 | 0.9489 | 0.9153 | 0.8058 | 0.5450 | 0.4672 | 0.4538 |
| RNFL defect | 0.9100 | 0.8870 | 0.8523 | 0.7579 | 0.8478 | 0.8734 | 0.7233 | 0.4024 | 0.4801 | 0.2838 |

FIG. 8

METHOD FOR CLASSIFYING FUNDUS IMAGE OF SUBJECT AND DEVICE USING SAME

CROSS-REFERENCE TO RELATED APPLICATIONS

This application is a national stage application of PCT/KR2019/004288 filed on Apr. 10, 2019, which claims priorities of Korean patent application number 10-2018-0062475 filed on May 31, 2018. The disclosure of each of the foregoing applications is incorporated herein by reference in its entirety.

TECHNICAL FIELD

The present invention relates to a method of classifying a fundus image and an apparatus using the same. In detail, using a method according to the present invention, a computing apparatus acquires the fundus image of the subject, generates classification information of the fundus image, generates an interpretation text based on the classification information, and provides the interpretation text to an external entity.

RELATED ART

A fundus image refers to an image used by ophthalmologists to specify abnormal lesions for diagnosing a disease. Currently, convolutional neural networks have many successful examples in classifying images. However, it simply aims at accurate diagnosis of a specific disease, such as diabetic retinopathy and diabetic macular edema. Appropriate lesion visualization and localization (specifying a relevant area in the image) to verify the contents of the diagnosis may not be provided. The present disclosure is to provide an architecture of a convolutional neural network that may classify the contents of individual findings and, at the same time, may localize lesions. According to the present inventors, the neural network architecture may be trained through regional annotations that enable better localization and classification in some findings.

A fundus image provides rich visual cues about a condition of an eyeball. In terms of analysis, an ophthalmologist searches for abnormal visual features, called findings, from the image and uses medical knowledge to determine diagnosis content based on the found findings. For example, severity of diabetic retinopathy (DR) is clinically determined based on presence of relevant findings and scope thereof {microaneurysm, hemorrhage, hard exudate, and cotton wool patch, etc.}.

Currently, a convolutional neural network (CNN) has reached the level of occupational ophthalmologists in diagnosing diabetic retinopathy (DR) and diabetic macular edema (DME). Here, CNNs in documents are trained to directly derive the diagnosis content, which differs from the diagnosis by an actual ophthalmologist. So far, there have been several studies to visualize findings that contribute to judging medical images. However, the individual findings are not distinguished from each other.

Previously, segmentation methods using hand-crafted feature-extractors were proposed to detect hemorrhage, hard exudate, drusen deposits, and cotton wool patch. However, heuristic feature-extractors contain bias of a human designer that considers visual properties of target findings and thus, do not well detect unpredictable patterns. That is, the performance thereof is seriously limited in application to the real world. A CNN for segmentation or detection may improve the performance, however, passive annotations for lesions are highly labor intensive, which is further intensive when the lesions are scattered across images. Accordingly, a data collection procedure becomes very expensive.

The present disclosure proposes a further inexpensive and effective approach that may collect regional annotations about findings from a fundus image and, at the same time, also proposes a CNN architecture that may classify presence of target findings and may localize lesions.

PRIOR ART DOCUMENT (Patent Document 1) KR10-1848321 B
(Patent Document 2) KR10-1848322 B

DETAILED DESCRIPTION

Technical Subject

The present invention is to accurately determine whether an image is interpretable from a fundus image, whether the image is normal or abnormal, and findings about abnormality, and also to automatically generate an interpretation text based on the findings and to provide the interpretation text for convenience on the medical field.

Also, the present invention is to further accurately localize a lesion associated with findings and also to improve the classification performance by training using guidance through regional cues.

To this end, the present invention is to enable regional guidance such that a neural network may learn correct patterns about findings instead of bias in an image.

Solution

Characteristic constitutions of the present invention to accomplish the aforementioned objectives and to achieve characteristic effects of the present invention are as follows:

According to an aspect of the present invention, there is provided a method of classifying a fundus image of a subject, the method including (a) acquiring, by a computing apparatus, or supporting another apparatus interacting with the computing apparatus to acquire the fundus image of the subject; (b) generating, by the computing apparatus, or supporting generating of classification information of the fundus image; and (c) generating, by the computing apparatus, or supporting generating of an interpretation text based on the classification information; and (d) providing, by the computing apparatus, or supporting providing of the interpretation text to an external entity.

According to another aspect of the present invention, there is provided a computer program stored in a non-transitory computer-readable record medium storing instructions to computer-implement the method according to the present invention.

According to still another aspect of the present invention, there is provided a computing apparatus for classifying a fundus image of a subject, the apparatus including a communicator configured to acquire the fundus image of the subject; and a processor configured to perform or supporting another apparatus interacting through the communicator to perform (i) a process of generating classification information of the fundus image; (ii) a process of generating an interpretation text based on the classification information; and (iii) a process of providing the interpretation text to an external entity.

Effects

According to the present invention, it is possible to provide convenience by automatically generating an interpretation text based on findings calculated from a fundus image.

According to an example embodiment of the present invention, it is possible to improve the classification performance of a neural network by training using guidance through regional cues.

The effects according to the example embodiment of the present invention may apply to various modalities of two-dimensional (2D) images or three-dimensional (3D) images as well as a fundus image, and particularly, may be used as is in a system of an ultrasound image, a computed tomography (CT) image, an magnetic resonance imaging (MRI) image, and the like, as well as an X-ray image conventionally used in a hospital. Accordingly, the method of the present invention is not subject to a specific modality image or platform.

BRIEF DESCRIPTION OF DRAWINGS

Example embodiments of the present invention will be described in more in detail with reference to the following figures that are simply a portion of the example embodiments and those of ordinary skill in the art to which the present invention pertains may readily acquire other figures based on the figures without an inventive work being made.

BEST MODE

The following detailed description of the present invention is described with reference to the accompanying drawings in which specific example embodiments of the present invention are illustrated as examples, to fully describe purposes, technical solutions, and advantages of the present invention. The example embodiments are described in detail enough for those skilled in the art to carry out the present invention.

The terms "image" and "image data" used throughout the detailed description and the claims herein refer to multi-dimensional data that includes discrete image factors (e.g., a pixel in a two-dimensional (2D). For example, the term "image" may refer to an image visible with an eye (e.g., displayed on a video screen) or a digital representation of an image (e.g., a file corresponding to a pixel output of computed tomography (CT), a magnetic resonance imaging (MM) detector, and the like).

For example, the term "image" may refer to a medical image of a subject collected by CT, MM, an ultrasound system, or known other medical imaging systems in the related art. The image may not necessarily need to be provided in terms of medical context and may be provided in terms of non-medical context, for example, X-rays for security screening.

For clarity of description, although some example image modalities are illustrated in the drawings, it will be apparent to those skilled in the art that image forms used in various example embodiments may include MRI, CT, positron emission tomography (PET), PET-CT, single-photon emission computed tomography (SPECT), SPECT-CT, MR-PET, three-dimensional (3D) ultrasound image, and the like, but are not limited to a specific form listed as the examples.

The term "Digital Imaging and Communications in Medicine (DICOM)" standard used throughout the detailed description and the claims is a generic term for a plurality of standards used for digital image representation and communication in medical devices. The DICOM standard is published by the American College of Radiology (ACR) and the National Electrical Manufacturers Association (NEMA).

Also, the term "Picture Archiving and Communication System (PACS)" used throughout the detailed description and the claims of the present invention is a term for systems that perform storage, processing, and transmission according to the DICOM standard. A medical image acquired using digital medical imaging equipment, such as X-ray, CT, and MM, may be stored in a DICOM format and may be transmitted to a terminal inside or outside a hospital over a network. Here, interpretation results and medical records may be added to the medical image.

Further, the term "localization" and modification thereof used through the detailed description and the claims refer to verifying, specifying, and embodying a location. For example, "localizing an area" refers to embodying a location of the area.

Also, the terms "comprises/includes" and modification thereof used throughout the detailed description and the claims are not intended to exclude other technical features, additions, components, or operations. Also, the term "single" or "one" refers to representing at least one and "still another" is not limited to at least second or more.

Those skilled in the art may clearly understand a portion of other purposes, advantages, and features of the present invention from this specification and another portion thereof from implementations of the present invention. The following examples and drawings are provided as examples only and not to limit the present invention. Therefore, detailed description described herein related to a specific structure or function is not limited and may be clearly understood by those skilled in the art as representative basic materials to provide a guideline for variously implementing the present invention as substantially suitable detailed structures.

Further, the present invention may include any possible combinations of example embodiments described herein. It should be understood that, although various example embodiments differ from each other, they do not need to be exclusive. For example, a specific shape, structure, and feature described herein may be implemented as another example embodiment without departing from the spirit and scope of the present invention. Also, it should be understood that a position or an arrangement of an individual component of each disclosed example embodiment may be modified without departing from the spirit and scope of the present invention. Accordingly, the following detailed description is not to be construed as being limiting and the scope of the present invention, if properly described, is limited by the claims, their equivalents, and all variations within the scope of the claims. In the drawings, like reference numerals refer to like elements throughout.

Unless the context clearly indicates otherwise, the singular forms "a," "an," and "the," are intended to include the plural forms as well. Also, when description related to a known configuration or function is deemed to render the present invention ambiguous, the corresponding description is omitted.

Regional annotations of findings about macular-centered images, which are used to verify a method according to the present invention described below, are collected using a data collection system as disclosed in Korean Patent Registration No. 10-1848321 and No. 10-1848322. An annotator may select a type of findings through a predetermined interface and may select regions corresponding thereto. If an eyeball present in an image is normal, there is no annotation about any findings on the image. As disclosed in the aforementioned registered patents, an image may be divided into eight areas and the respective areas reflect the anatomical structure of the eyeball and regional characteristics of findings. For example, such areas may include a macular area, a superiordisc area, an inferior disc area, a temporal area, a superotemporal area, an inferotemporal area, a superonasal area, and an inferonasal area.

Figure 1:
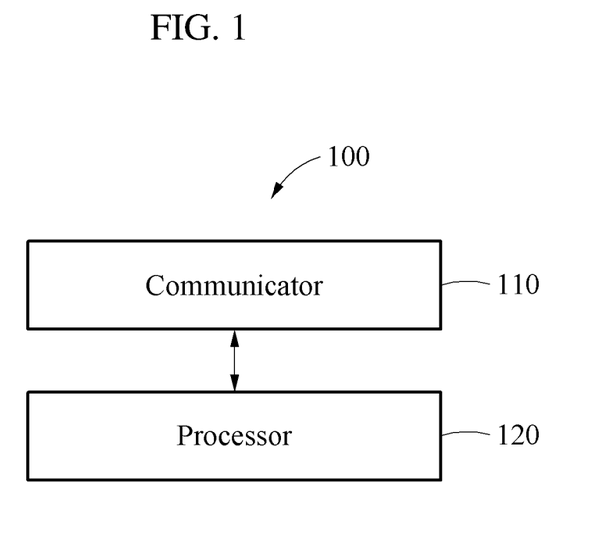
FIG. 1 is a diagram illustrating an example of a computing apparatus configured to perform a method (hereinafter, a "fundus image classification method") of classifying a fundus image of a subject according to the present invention.

FIG. 1 is a diagram illustrating an example of a computing apparatus configured to perform a fundus image classification method according to the present invention.

Referring to FIG. 1, a computing apparatus 100 according to an example embodiment of the present invention includes a communicator 110 and a processor 120, and may directly or indirectly communicate with an external computing apparatus (not shown) through the communicator 110.

In detail, the computing apparatus 100 may achieve a desired system performance using a combination of typical computer hardware (e.g., an apparatus including a computer processor, a memory, a storage, an input device and an output device, components of other existing computing apparatuses, etc.; an electronic communication apparatus such as a router, a switch, etc.; an electronic information storage system such as a network-attached storage (NAS) and a storage area network (SAN)) and computer software (i.e., instructions that enable a computing apparatus to function in a specific manner).

The communicator 110 of the computing apparatus may transmit and receive a request and a response with another interacting computing apparatus. As an example, the request and the response may be implemented using the same transmission control protocol (TCP) session. However, it is provided as an example only. For example, the request and the response may be transmitted and received as a user datagram protocol (UDP) datagram. In addition, in a broad sense, the communicator 110 may include a keyboard, a mouse, and other external input devices to receive a command or an instruction.

Also, the processor 120 of the computing apparatus may include a hardware configuration, such as a micro processing unit (MPU), a central processing unit (CPU), a graphics processing unit (GPU), a neural processing unit (NPU) or a tensor processing unit (TPU), a cache memory, a data bus, and the like. Also, the processor 120 may further include a software configuration of an application that performs a specific objective, an operating system (OS), and the like.

Figure 2:
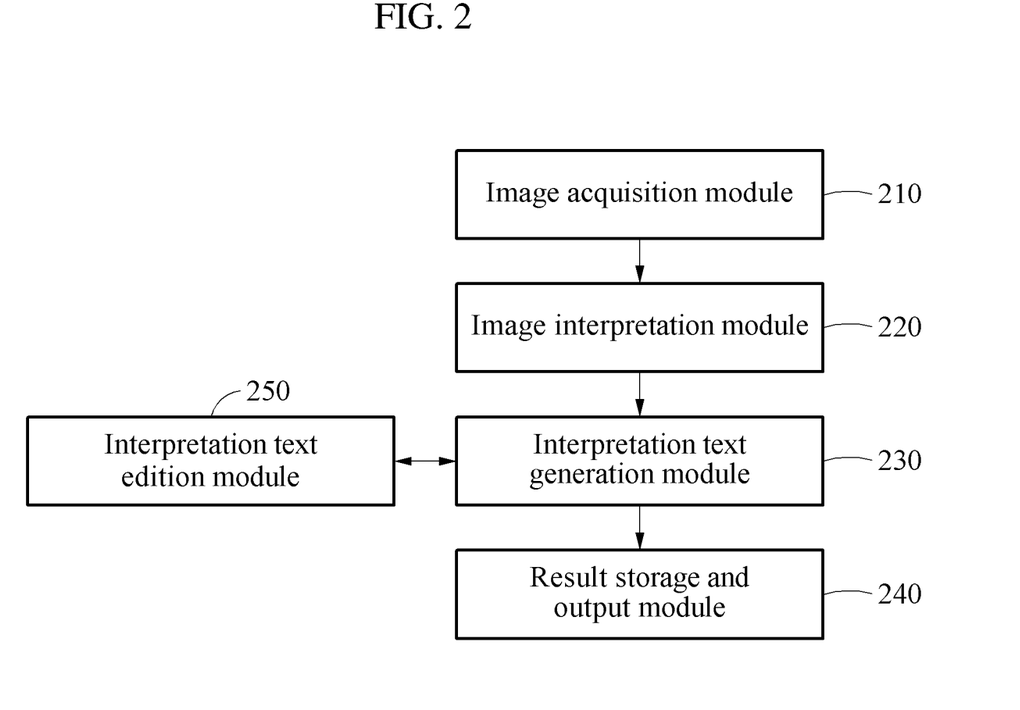
FIG. 2 is a diagram illustrating an example of hardware or software components of a computing apparatus configured to perform a fundus image classification method according to the present invention.

FIG. 2 is a diagram illustrating an example of hardware or software components of a computing apparatus configured to perform a fundus image classification method according to an example embodiment.

Describing a method and a configuration of an apparatus according to the present invention with reference to FIG. 2, the computing apparatus 100 may include an image acquisition module 210 as a component. The image acquisition module 210 is configured to acquire a medical image to which the method according to the present invention applies. An image interpretation module 220 is used to interpret a fundus image acquired by the image acquisition module 210.

It will be apparent to those skilled in the art that individual modules of FIG. 2 may be configured through, for example, the communicator 110 or the processor 120 included in the computing apparatus 100, or through interaction between the communicator 110 and the processor 120.

The fundus images may be acquired from an external image storage system, such as, for example, a photographing device interacting through the communicator 110 or Picture Archiving and Communication System (PACS). However, it is provided as an example only. For example, the fundus images may be captured by a (medical) imaging device and transmitted to the PACS according to the DICOM standard and then, acquired by the image acquisition module 210 of the computing apparatus 100.

For learning for a model of the image interpretation module 220, labeling information about a fundus image may be acquired with the fundus image. During learning, the fundus image and the labeling information are used to pretrain an image interpretation model included in the image interpretation module 220. The labeling information may include information about findings corresponding to the fundus image and an area corresponding to the findings and may include additional information, such as locations of macular and optic disc.

The trained image interpretation model may generate classification information of the fundus image in the image interpretation module 220 and may transfer the classification information to an interpretation text generation module 230 and a result storage and output module 240. The interpretation text generation module 130 may generate an interpretation text based on the classification information and the result storage and output module 240 may provide an external entity with classification results about the fundus image through a user interface displayed on a predetermined output device, for example, a display. For convenience of a user, an interpretation text edition module 250 capable of editing the generated interpretation text may be further provided.

Here, the external entity may be understood to include a user of the computing apparatus 100, a manager, and medical staff in charge of a subject present in the fundus image and, in addition thereto, any types of entities that require the classification of the image, that is, determination (interpretation) of classification.

Functions and effects of components shown in FIG. 2 are further described below. Although the components of FIG. 2 are illustrated in a single computing apparatus for clarity of description, the computing apparatus 100 that performs the method of the present invention may be configured such that a plurality of apparatuses may interact with each other, which is described in the claims attached herein.

Hereinafter, a fundus image classification method according to the present invention is further described with reference to FIG. 3, FIG. 4, and FIG. 5.

Figure 3:
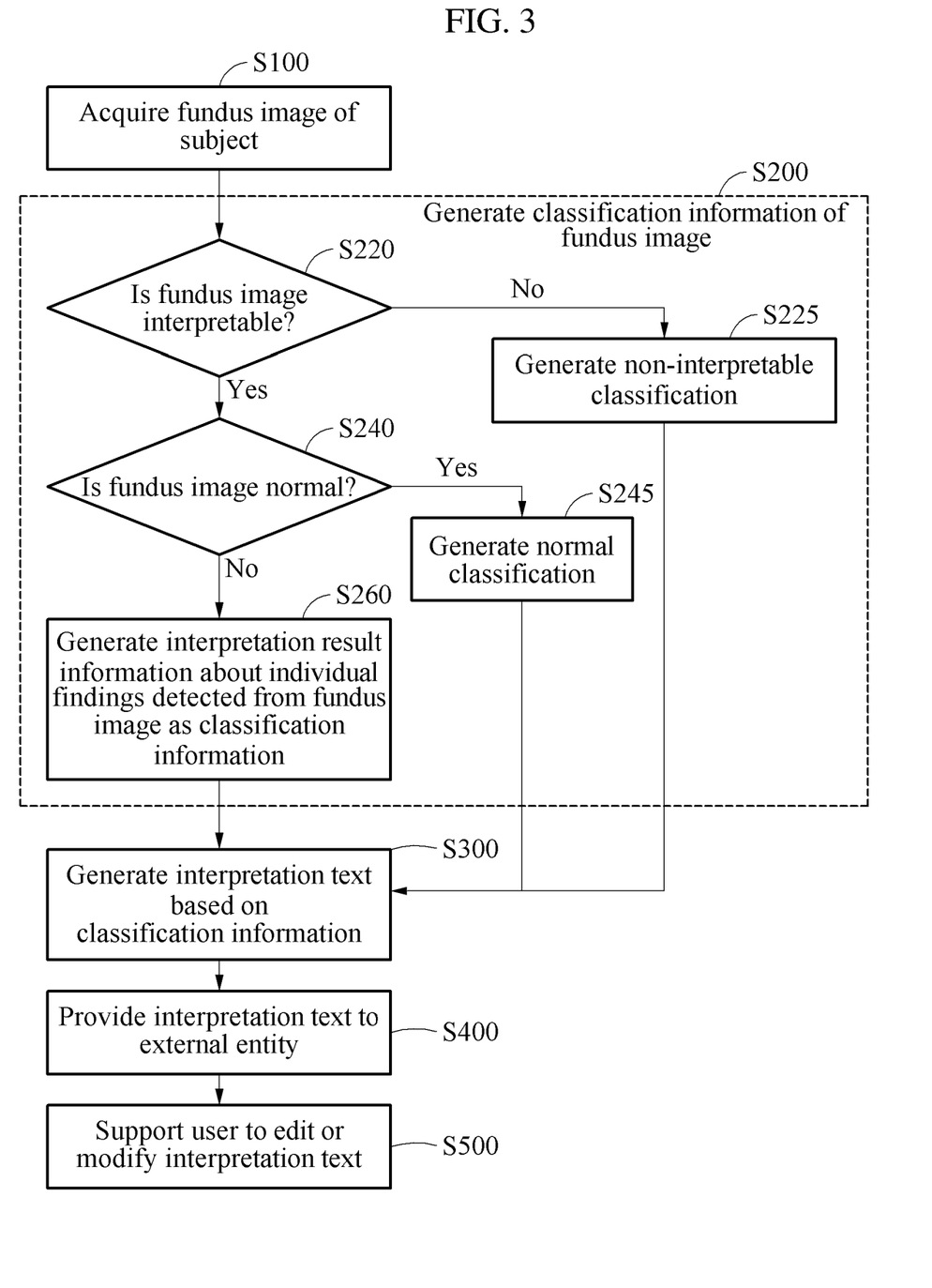
FIG. 3 is a flowchart illustrating an example of a fundus image classification method according to the present invention.
Figure 4:
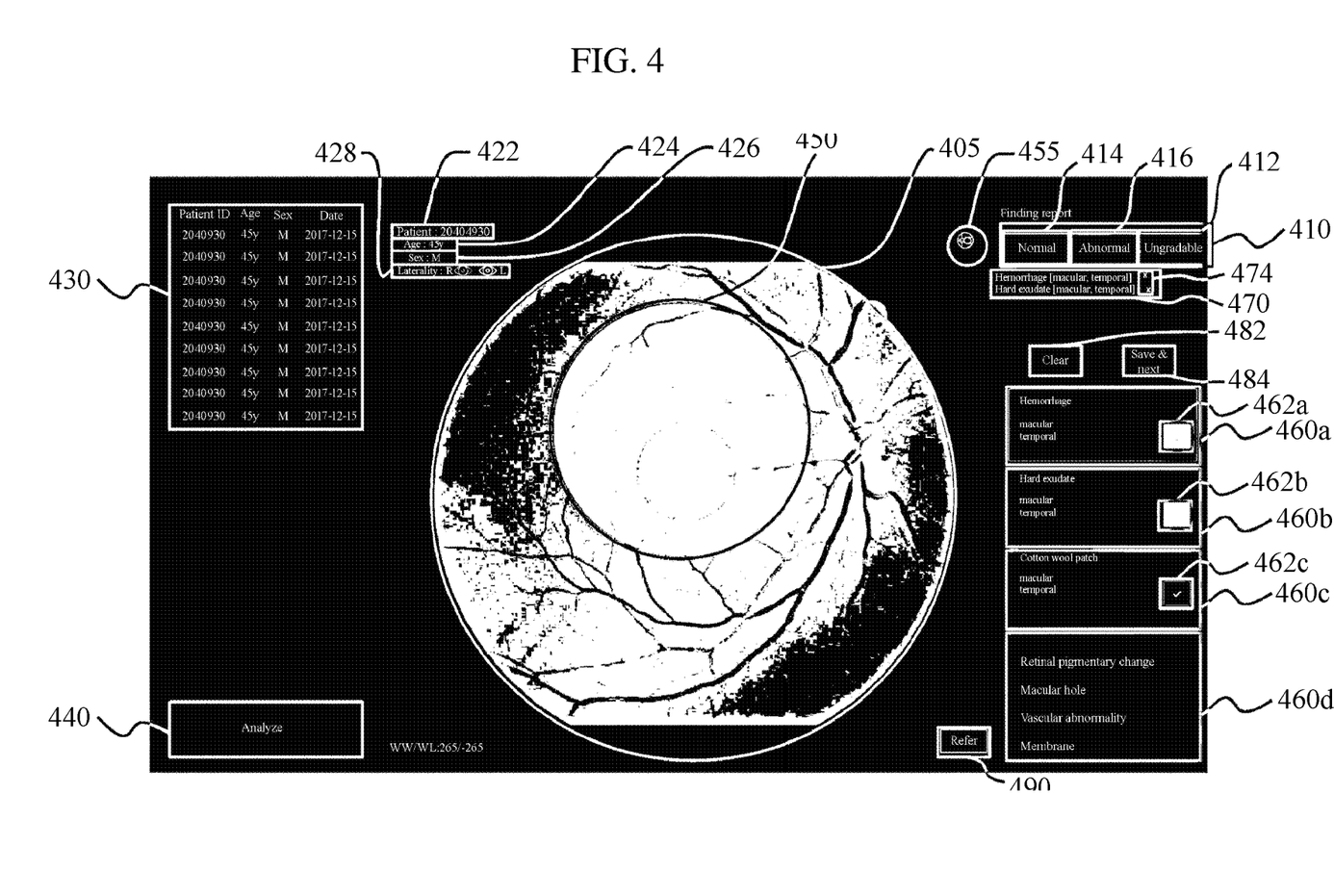
FIG. 4 illustrates an example of a user interface available for a fundus image classification method of the present invention.

FIG. 3 is a flowchart illustrating an example of a fundus image classification method according to the present invention, and FIG. 4 illustrates an example of a user interface available for a fundus image classification method of the present invention.

Referring to FIG. 3, the fundus image classification method according to the present invention includes operation S100 of acquiring, by the image acquisition module 210 implemented by the computing apparatus 100, or supporting another apparatus (not shown) interacting through the communicator 110 of the computing apparatus 100 to acquire a fundus image of a subject.

The fundus image classification method according to the present invention further includes operation S200 of generating, by the image interpretation module 220 implemented by the computing apparatus 100, or supporting generating of the classification information of the fundus image. Here, the classification information corresponds to findings about the fundus image and visualization information that supports the classification information may also be generated together. The visualization information may be provided as an activation map, which is described below.

In an example embodiment, operation S200 includes, in detail, operation S220 of supporting, by the image interpretation module 220, or supporting the other apparatus through the communicator 110 to determine whether the fundus image is interpretable.

As illustrated in FIG. 4, through a user interface provided to perform the method according to the present invention, a fundus image 405 and the interpretability of the fundus image may be displayed.

When the fundus image is uninterpretable in operation S220, an non-interpretable classification may be generated as the classification information, for example, an indication 412 "Ungradable (which indicates uninterpretable)" of FIG. 4.

Referring to the example of FIG. 4, for convenience of a user, that is, a interpreter, information of the subject (patient) including at least one of an identification number of the (Patient ID) 422, an age (Age) 424, a gender (Sex) 426, and binocular classification information (Laterality) 428 of a fundus image of the subject may be provided to the user. Also, a list 430 of a plurality of subjects may be provided and a predetermined interface element, such as an "Analyze" button 440 of FIG. 4 may be provided to perform operation S200 with a simple manipulation.

Operation S200 further includes operation S240 of calculating, by the image interpretation module 220, or supporting calculating of normality information that determines whether the fundus image is normal or abnormal and a confidential level of the normality information from the fundus image when the fundus image is interpretable.

When the fundus image is normal in operation S240, normality classification may be generated as the classification information. For example, referring to FIG. 4, when the fundus image is normal, it may be displayed as "Normal" or may be highlighted 414.

Operation S200 further includes operation S260 of generating, by the image interpretation module 220, or supporting the other apparatus to generate interpretation result information about individual findings detected from the fundus image and a confidential level of the individual findings as the classification information when the fundus image is abnormal.

In operation S260, the locations of the individual findings may be calculated as the aforementioned activation map using the calculation method in the following, which is illustrated as a reference numeral 450 in FIG. 4.

Referring to FIG. 4, when the fundus image is abnormal (Abnormal) 416, a list of detected individual findings may include Hemorrhage 460a, Hard Exudate 460b, Cotton Wool Patch 460c, and the like. Here, a location corresponding to the selected individual findings (e.g., Hemorrhage of FIG. 4) may be highlighted. For example, the activation map 450 corresponding to the selected findings is illustrated as an example in the figure. However, it is provided as an example only and various types of displaying a list of individual findings and an activation map may be used.

Also, referring to FIG. 4, a predetermined interface element 455 may be further provided to display or hide a division line for classifying an area (e.g., by toggle) on the user interface.

In addition, a predetermined interface element 456 (not shown) may be further provided to display or hide the entire activation map.

When the list of detected individual findings (460a to 460c) is displayed, information (e.g., "Macular" (a macular area) and "Temporal" (a temporal area)) of areas where the individual findings appear may also be provided. An interface element 457 (not shown) capable of displaying or hiding an activation map for each of the individual findings {e.g., by toggle} may be further provided.

A list of undetected individual findings 460d may also be provided as illustrated in FIG. 4.

Meanwhile, as disclosed in Korean Patent Registration No. 10-1848321 and No. 10-1848322, locations of macular and optic disc may be automatically detected from a fundus image for reference in generation of individual findings. In addition, as a neural network architecture conceived to detect the locations of the macular and the optic disc, an example neural network architecture having excellent performance compared to that of a conventional neural network is further described below. In operation S260, when the locations of the macular and the optic disc are detected, the image interpretation module 220 may divide or support the other apparatus to divide an area of the fundus image (e.g., into eight areas) by referring to the detected locations.

Referring again to FIG. 3, the fundus image classification method according to the present invention further includes, after operation S200, operation S300 of generating, by the interpretation text generation module 230 implemented by the computing apparatus 100, supporting the other apparatus to generate an interpretation text based on the classification information. The term "interpretation text" herein is a term intended to be expressed in a form of a sentence and also in a form in which information is briefly arranged in words.

In the example embodiment in which operation S260 is performed, in operation S300, it is possible to generate or support the other apparatus to generate the interpretation text representing the locations of the individual findings based on the divided areas.

Here, the interpretation text may be generated, as an initial value thereof, (i) a basic interpretation text provided when a fundus image is normal or (ii) a selective interpretation text that is a result selected based on the classification information from among at least one set of a plurality of interpretation text selections provided corresponding to individual findings when the fundus image is abnormal.

Referring to FIG. 4, an example of an interpretation text 470 of the fundus image is provided. For example, at least one of a type of abnormal findings found in the fundus image, a name of individual findings (e.g., 'hemorrhage,' 'hard exudate,' etc.), a confidential level thereof, and a name of an area where the individual findings are observed (e.g., 'macular,' 'temporal,' etc.) may be included in information of the interpretation text.

For example, the type of anormal findings included in the interpretation text may include "retinal abnormality," "glaucoma abnormality," "optic nerve abnormality, etc., the individual findings may include hemorrhage, hard exudate, cotton wool patch, drusen & drusenoid deposits, and retinal pigmentary change. However, they are provided as an example only, the individual findings may also include a macular hole, vascular abnormality, membrane, fluid accumulation, chroioretinal atrophy/scar, choroidal lesion, a myelinated nerve fiber, RNFL defect, galucomatous disc change, non-glaucomatous disc change, other findings or artifacts, and the like.

When the interpretation text is generated in operation S300, the fundus image classification method according to the present invention further includes operation S400 of providing, by the result storage and output module 240 implemented by the computing apparatus 100, or supporting the other apparatus to provide the interpretation text to the external entity. For example, for this reference, a "Refer" button 490 may be provided as in the example interface of FIG. 4.

Figure 5:
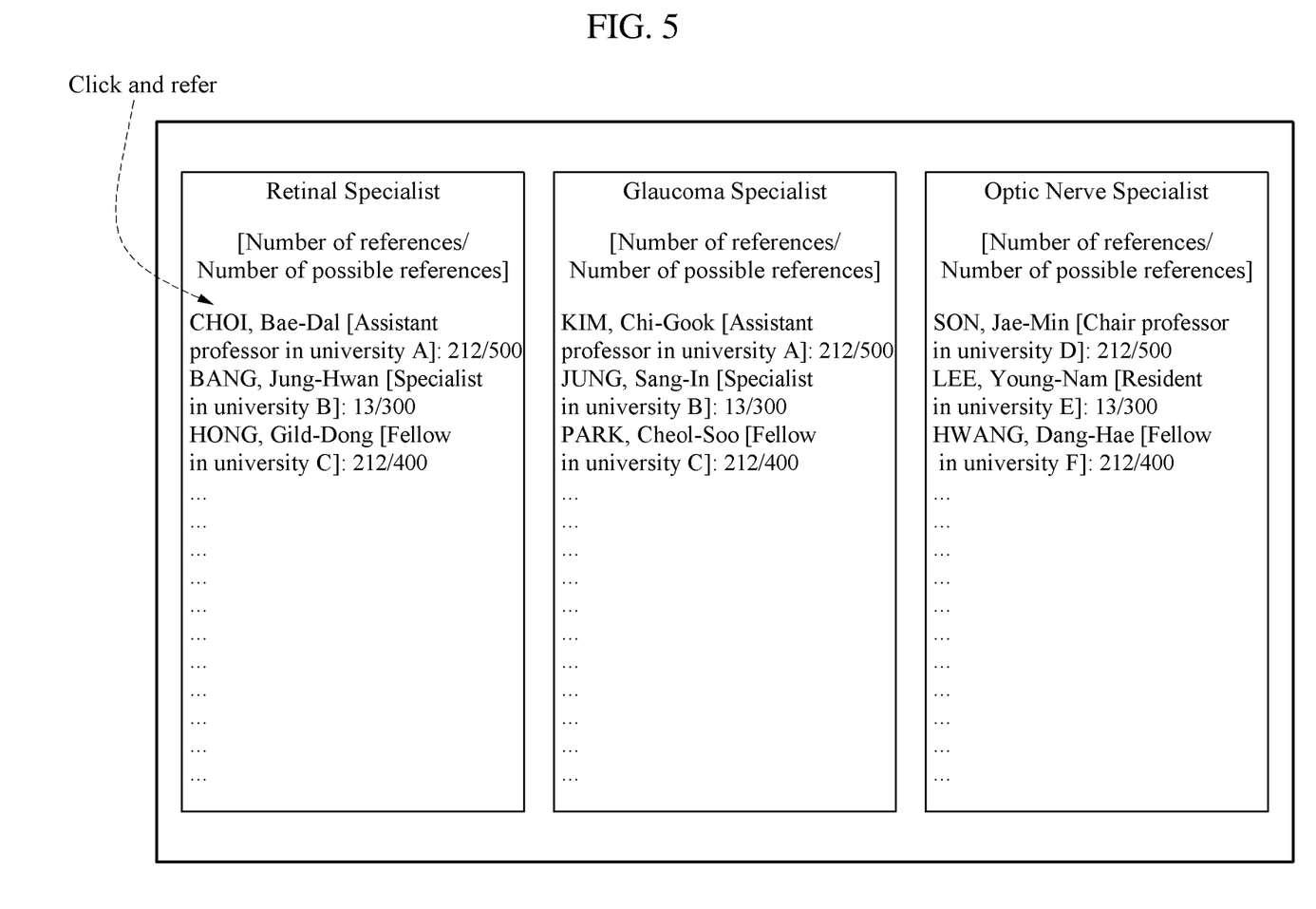
FIG. 5 illustrates an example of a user interface that allows an external entity to refer to an interpretation text generated according to a fundus image classification method of the present invention.

FIG. 5 illustrates an example of a user interface provided such that an external entity may refer to an interpretation text generated according to a fundus image classification method of the present invention. Referring to FIG. 5, a user interface that allows an expert in each field to request to refer to interpretation result information and an interpretation text that are results according to a method of the present invention as an external entity. For example, a specialization field, a name, a position, an affiliation, a number of possible references, and a number of references, may be provided on the user interface as listings of the external entity.

Meanwhile, the generated interpretation text may need to be modified or edited. Therefore, the fundus image classification method according to the present invention may further include, after operation S400, operation S500 of providing, by the interpretation text edition module 250 implemented by the computing apparatus 100, a predetermined user interface and supporting the user to edit or modify the interpretation text through the user interface. In operation S500, in response to receiving a modification input, the interpretation text edition module 250 may modify or support the other apparatus to modify the interpretation text.

For example, if a manipulation of a predetermined selectable interface element {e.g., check buttons 462a, 462b, and 462c of FIG. 4} to apply or not apply individual findings to the interpretation text is acquired as the modification input, the interpretation text may be modified accordingly.

For example, in response to a manipulation associated with individual findings included in the list of undetected individual findings 460d (e.g., a manipulation of clicking on a name of individual findings blurrily displayed as in FIG. 4), individual findings included in the list of undetected individual findings may be switched to be detected.

Also, for example, for the modification input, a deletion ("Clear") button 482 for deleting the entire content of the interpretation text and a save and next subsequent reading ("Save&Next") button 484 for storing the content of a currently provided interpretation text and performing the method of the present invention on the next subject may be provided. An individual deletion element 474 for deleting the content on individual findings included in the interpretation text may also be provided.

As an example of the user interface used in the present disclosure, a graphical user interface (GUI) includes one or more display images generated by a display processor, which enables user interaction with the processor or another apparatus and functions of acquiring and processing related data. Also, the GUI includes an executable procedure or an executable application. The executable procedure or the executable application allows the display processor to generate signals that represent the GUI display images based on a condition. The signals are transferred to a display device configured to display images to be viewed by the user. The processor manipulates the GUI display images in response to signals received from input devices under control of the executable procedure or the executable application. In this manner, the user may interact with the display image using the input devices. It will be understood by those skilled in the art that the user interaction with the processor or the other apparatus is enabled.

The term "user" described herein may refer to a plurality of users for the purpose of acquiring rich and overlapping medical images and relevant data instead of simply referring to a singular form. Therefore, there may be an intent to secure the integrity of a fundus image in learning of the fundus image or actual clinical use.

Various types of classifiers may be used as a interpretation model of the image interpretation module 220 used for the method according to the present invention. For example, the interpretation model may include a deep learning model, a random forest, and a Bayesian image acquisition module. Hereinafter, an example of a neural network architecture used as a interpretation model by the present inventors is described with reference to FIG. 6.

Figure 6:
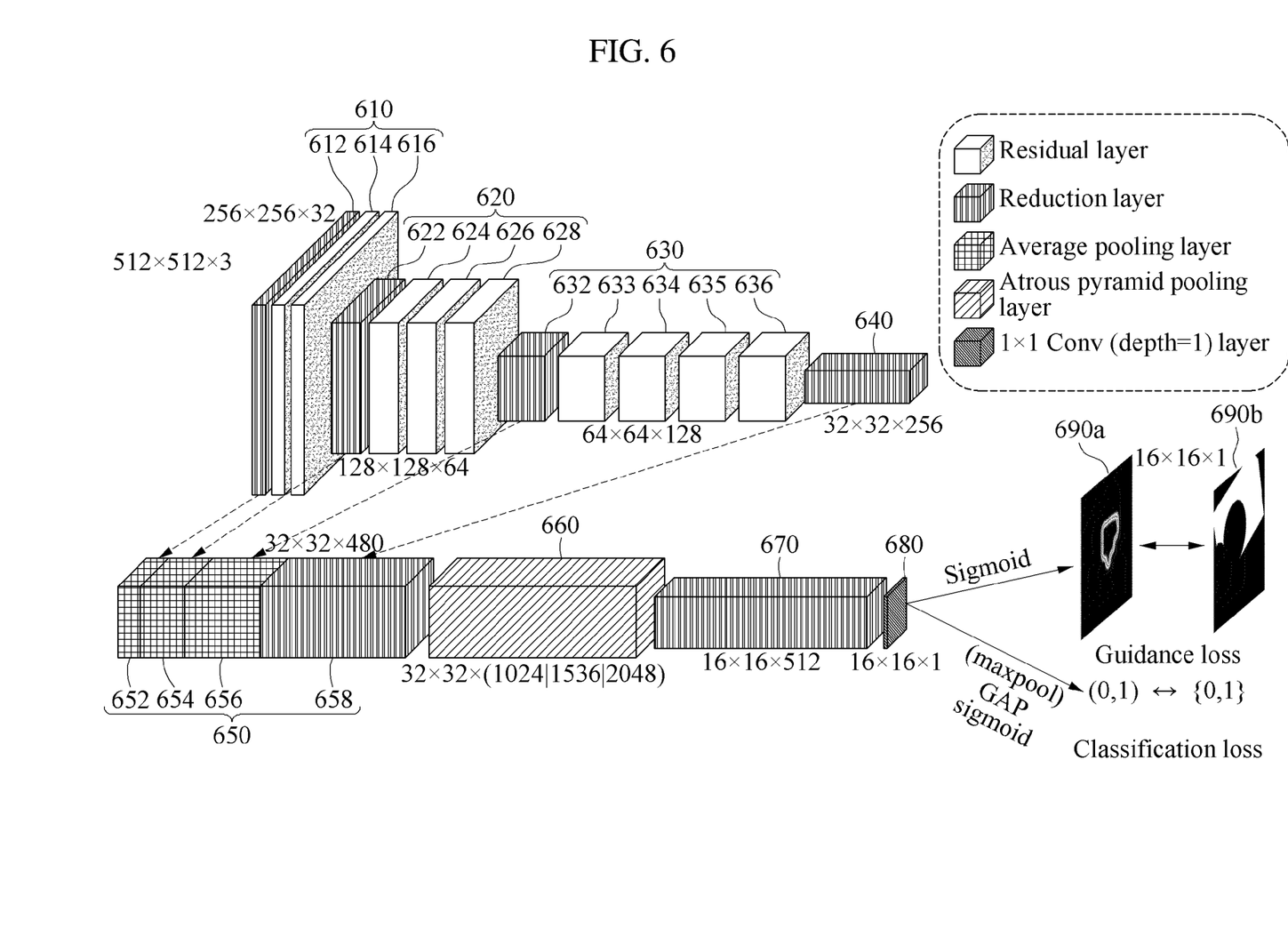
FIG. 6 is an example of a neural network architecture according to an example embodiment of the present invention.

Example Neural Network Architecture of the Present Invention FIG. 6 illustrates an example of a neural network architecture according to an example embodiment of the present invention.

Referring to FIG. 6, the neural network architecture according to the example embodiment may include residual layers 612, 622, 632, 640, 658, and 670 (feature maps after a residual unit), reduction layers 614, 616, 624, 626, 628, 633, 634, 635, and 636 {3×3 convolution of stride 2, batch-norm, feature maps after ReLU}, average pooling layers 652, 654, and 656, an atrous pyramid pooling layer 660 and a 1×1 convolution (depth=1, 680) layer. Here, the terms "residual layer" or "residual unit" refer to feature maps in which an input layer is added to an output layer with respect to {convolution, batch-norm, ReLU}×2.

As a layer becomes deeper, it is advantageous to monotonically increase a number of layers constituting each of convolution blocks 610, 620, and 630. If the number of layers is identical or less, the performance may be degraded with the same parameter. Meanwhile, although FIG. 6 illustrates a total of three convolution blocks as an example, it is provided as an example only and a more number of convolutions blocks may be used.

When the height and the width are halved, the depth of layers are doubled. First four or more reduction layers having different sizes are concatenated with the average pooling and use all of a low level feature and a high level feature. That is, according to the neural network architecture of the example embodiment, various levels of features may be extracted by extracting features through a plurality of convolutions and by performing concatenation in a depth direction through fitting the resolution to be identical using an operation of compressing information with resizing (e.g., average pooling). Referring to the example of FIG. 6, the reduction layers of reference numerals 612, 622, and 632 are concatenated into reference numerals 652, 654, and 656, respectively, through resolution adjustment. Here, the reduction layer of reference numeral 640 is concatenated therewith.

The concatenated feature maps are atrous-pyramid-pooled 660 at a dilation rate of 1, 2, 4, 8 (findings about a large scale), a dilation rate of 1, 2, 4 (findings about an intermediate scale), or a dilation rate of 1, 2 (findings about a small scale). It is to effectively double receptive fields. That is, atrous pyramid pooling is employed to concatenate features to the receptive fields with various scales. A subsequent layer of the atrous pooling layer extracts features by reducing the resolution by two times with a convolution of stride 2.

The final layer 680 refers to the 1×1 convolution layer and operates the 1×1 convolution of the previous layer 670. It is noted that this is linear concatenation of previous feature maps as in a class activation map (CAM). Values of the layer are normalized to (0, 1) through a sigmoid function and accordingly, a subsequent layer may be regarded as a normalized activation map. An activation map 690a contrived by the present inventors differs from the CAM in that an additional loss function guides activation to appear only in exemplary areas only.

According to the experiment by the present inventors, concatenation of 16×16 features exhibited a most accurate activation map. Desirably, the final layer may have a size of 8×8 to 32×32, which is to match a size of an actual fundus image corresponding to 1×1 to a significant lesion identifiable size.

Also, one side of the 1×1 convolution layer is global average pooling (GAP) performed and normalized using the sigmoid function and thus, an estimate value considering a classification result, that is, presence or absence is calculated. The other side of the 1×1 convolution layer is an activation map normalized through sigmoid. Accordingly, the activation map is directly associated with prediction in the neural network architecture according to the present invention and a separate external operation for visualization is not required.

In the case of a small lesion area in a medical image, activation occurs at the same location in the activation map due to a false positive {bias appears}. To prevent this, an operation of outputting a non-decreasing function value about a maximum value of an activation value within a designated district such as maximum pooling may be performed before global average pooling (GAP).

An objective function according to an example embodiment of the present invention follows as: If a fundus image $I \in R^{W_I H_I}$ is given, presence of target findings in the image I is encoded to $y_{true} \in \{0, 1\}$ and a presence probability $y_{true} \in \{0, 1\}$ is output from a neural network. If K images are given as a mini-batch, binary cross-entropy about a classification loss of FIG. 6 is given as the following Equation 1.

$$L_{class}(y_{true}, y_{pred}) = \frac{1}{k}\sum_{i=1}^{k}[-y_{true}^{i}\log y_{pred}^{i} - (1-y_{true}^{i})\log(1-y_{pred}^{i})]$$ [Equation 1]

In Equation 1, $y_{true}=\{y_{true}^{1}, \ldots, y_{true}^{k}\}$ and $y_{pred}=\{y_{pred}^{1}, \ldots, y_{pred}^{k}\}$.

When final feature maps have the size of $W_F \times H_F$, a region mask 690b about the target findings $M \in \{0, 1\}^{W_F \times H_F}$ is given as a label and an activation map $A \in (0, 1)^{W_F H_F}$ is generated from the neural network. A guidance loss of FIG. 6 with the mini-batch with the size of k is given as the following Equation 2.

$$L_{guide}(A, M) = \frac{1}{kW_F H_F}\sum_{i=1}^{k}\sum_{l=1}^{W_F H_F}(1-m_l^i)\log(a_l^i + \epsilon)$$ [Equation 2]

In Equation 2n, $A=\{A^1, \ldots, A^k\}$, $M=\{M^1, \ldots, M^k\}$ and $m_l^i$ and $a_l^i$ respectively denote $l^{th}$ pixel values of $M^i$ and $A^i$ with respect to $l=1, \ldots, W_F H_F$. It is noted that, if $a_l^i \approx 0$, $\epsilon \geq 0$ is added to an inner side of log for numerical stability. Briefly describing, the guidance loss suppresses any activation in areas where mask value=0 and does not affect activation inside the mask. In Equation 2, $\log(\max(a_l^i, \epsilon))$ may be used instead of $\log(a_l^i + \epsilon)$ The guidance loss serves to decrease an activation value acquired when mask value=0. The backpropagation equation of W value is (1−a)*out when an output value of a previous layer is out and thus, increases according to a decrease in a value of a that is an activation value of each pixel. Accordingly, there is the effect of removing artifacts occurring at the edge in a process in which the classification loss finds a pattern.

Accordingly, a total loss value may be acquired by combining the classification loss using the loss function, for example, binary cross-entropy and the guidance loss multiplied with λ that is a hyperparameter for comprise with the classification loss, and is given as the following Equation 3.

$$L_{total} = L_{class}(y_{true}, y_{pred}) + \lambda L_{guide}(A, M)$$ [Equation 3]

That is, λ denotes a value for balancing between two objective functions.

Implementation Example of Neural Network Architecture of the Present Invention for Verification of Performance The present inventors selectively exhibited results about clinically important findings associated with DR and DME (hemorrhage, hard exudate, drusen, cotton wool patch (CWP)), a macular hole, a membrane, and retinal nerve fiber layer (RNFL) defect.

The present inventors separated annotations into a training set and a test set based on professional knowledge of annotators for measuring the performance of the neural network architecture. The training set was annotated by 27 licensed ophthalmologists and the test set was annotated by 16 accredited retinal specialists and 9 accredited glaucoma specialists. Each fundus image was annotated by a total of three ophthalmologists. Here, a total number of images included in the training set and a total number of images included in the test set were 66,473 and 15,451, respectively.

The training set was divided into a derivation set 90% and a verification set 10%. A model of the example neural network architecture according to the present invention was optimized with the derivation set until a verification loss was stagnated and exacerbated. A model with the lowest verification loss was tested with a test set regarded as gold standards. The present inventors determined that, when all of the ophthalmologists do not add annotations, target findings are absent, and when at least two of three ophthalmologists add annotations, target findings are present. The union of annotated areas was provided as regional cues during training.

The present inventors aimed to measure the effect of the guidance loss by experimenting example CNN architectures of the present invention that provide or do not provide regional guidance and by comparing results in terms of AIR of Area Under Receiver Operating Characteristic (AU-ROC) curve, specificity, sensitivity, and regional cues. AIR is defined as a value acquired by dividing an addition value of internal activations of the regional cues by an addition value of all of the activations. AIR was measured with respect to all of true positive and false negative in a classification when the regional cues are available. The present inventors implemented a neural network in which the regional guidance is present or absent by changing a value of $\lambda$ in Equation 3 based on the neural network architecture of FIG. 6 (if $\lambda=0$, no regional guidance).

Since original color fundus images used for the experiments were cropped to center a fundus portion, a black background was removed and the images were resized to have a size of 512×512 for a neural network input. Desirably, the images may be resized to have a size between 256×256 to 1024×1024. Pixel values of pixels that constituting the image may be divided by 255 to be included in the [0,1] range. Here, other preprocessing may not be required. When proceeding with learning in a situation in which a sufficiently large amount of data is given, it may be meaningful to control only the range of pixel values without performing preprocessing at all in the case of red-green-blue (RGB).

The resized images were randomly data-augmented by affine transformation (flip, resize, rotation, translation, and shear) and the intensity thereof was randomly re-scaled. Weights and biases were initialized using Xavier initialization. The present inventors used a stochastic gradient descent (SGD) having a nestrov momentum of 0.9 and a decaying learning rate as an optimizer. The batch size was set to 32 according to the recommendation that a small batch size is better for generalization. Also, the numerical stability was achieved by setting $\varepsilon=10^{-3}$ in Equation 2 and the classification loss and the guidance loss were treated in the same manner by setting $\lambda=1$ in Equation 3.

Meanwhile, for an image with a size of 512×512 or more, it is desirable to halve a resolution through a convolution of consecutive stride 2, which is to achieve efficient calculation.

Here, it will be understood by those skilled in the art that the present invention is not limited to a specific numerical number appearing in the example neural network.

Figure 7:
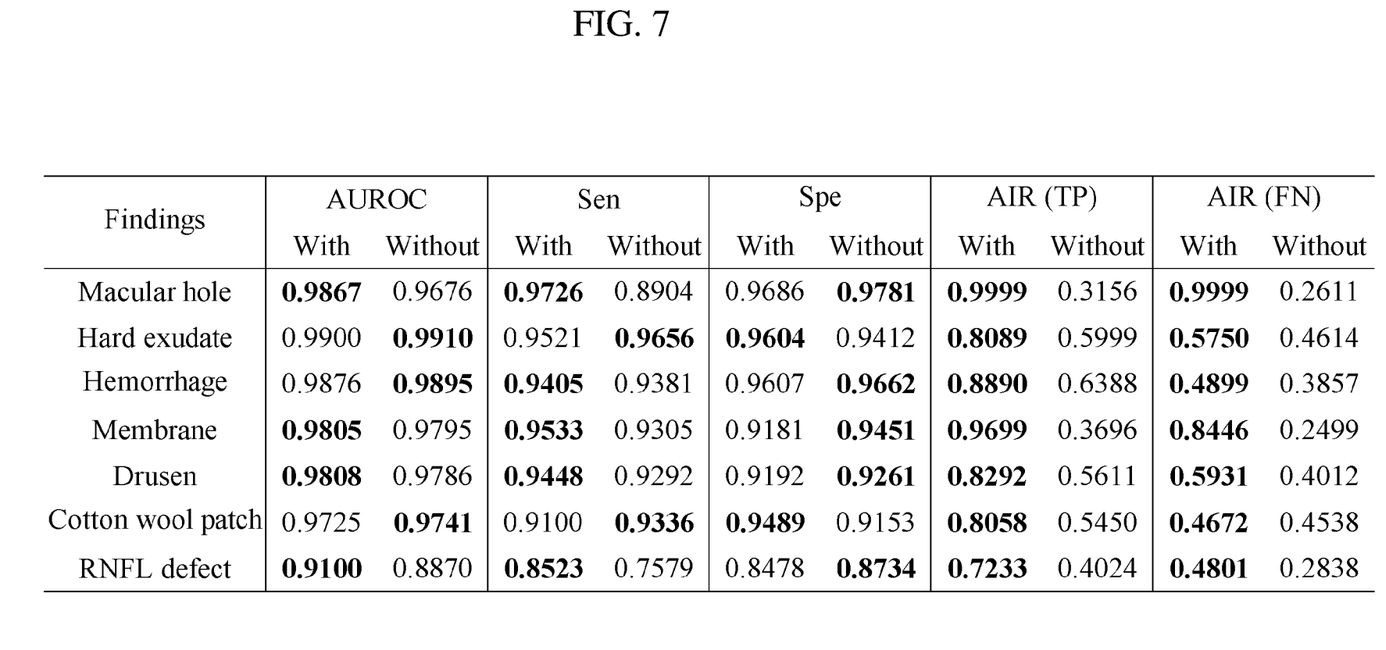
FIG. 7 is a table showing comparison results between the performance of a neural network architecture provided according to an example embodiment of the present invention and an architecture according to the related art.

Experiment Results by Implementation Example of Neural Network Architecture of the Present Invention FIG. 7 is a table showing results of comparing the performance of a neural network architecture provided according to an example embodiment of the present invention and an architecture according to the related art.

Referring to FIG. 7, results of comparing the performance between a model to which a guidance loss is introduced and a model in which the guidance model is absent are summarized as a table. The present inventors were able to verify the positive effect of the guidance loss about AIR of true positive (TP) and false negative (FN) over all of the findings. It is desirable in that the neural network may pay attention to regional cues for classification. Therefore, the neural network tends to less learn biases of a data set. Also, a difference in AIR between the two models is larger in TP than in FN. It is reasonable since FN includes cases in which classification of the neural network is difficult, whereas TP may be relatively easily classified with high confidence.

With respect to AU-ROC, significant enhancement was achieved only in a macular hole and a retinal nerve fiber layer (RNFL) defect. Such findings are observed in specific areas. Therefore, it may be interestingly notable that the greatest advantage appears by regional cues. It may be explained as learning easier by guiding the neural network to pay attention to areas that are important for classification. Meanwhile, findings scattered over a wide area, such as hemorrhage, hard exudate, and drusen, may have little benefit of regional cues in classification. The present inventors speculate that the guidance may be slightly redundant since the findings has wide regional cues, however, the guidance will be more important for a small lesion. When AU-ROC is higher, higher sensitivity and lower specificity are observed. However, there is a remarkable difference in the macular hole and the RNFL defect.

Figure 8:
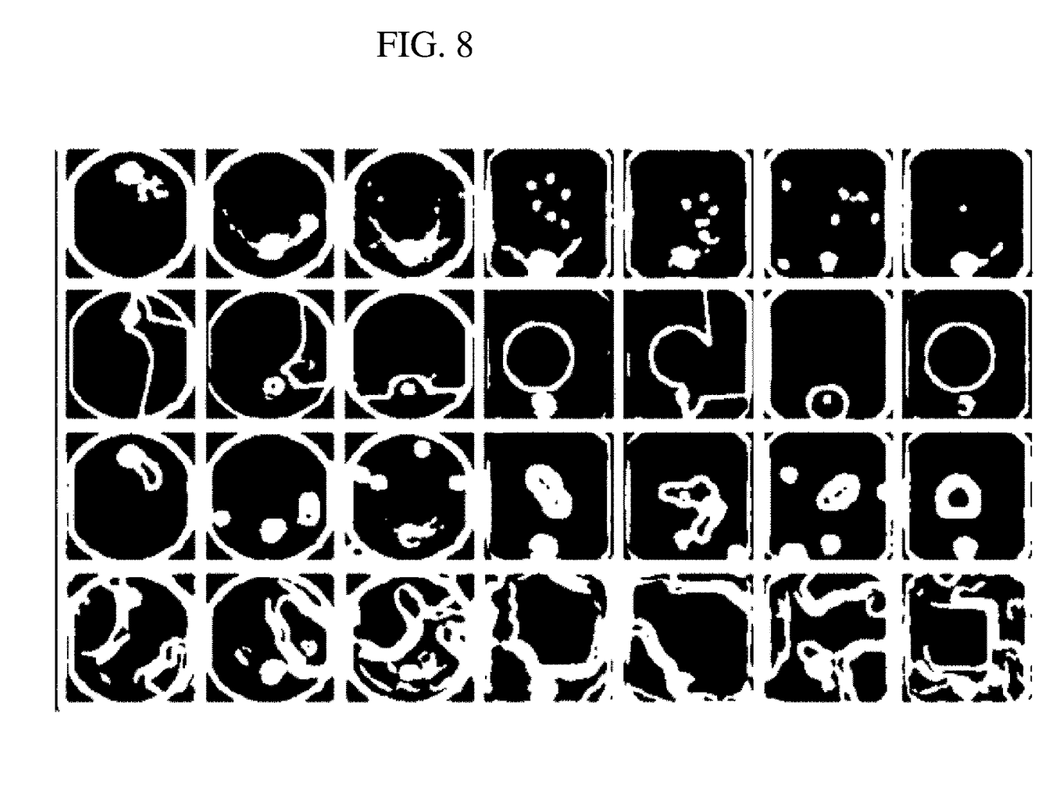
FIG. 8 illustrates an example of qualitatively comparing the performance of a neural network architecture provided according to an example embodiment of the present invention and an architecture according to the related art.

FIG. 8 illustrates an example of qualitatively comparing the performance of a neural network architecture provided according to an example embodiment of the present invention and an architecture according to the related art.

Referring to FIG. 8, activation maps of a neural network with a guidance loss and activation maps of a neural network without the guidance loss are compared. Before being overlapped on an original image, the activation maps are upscaled by double linear interpolation, blurred using a 32×32 Gaussian filter for natural visualization, and normalized to [0, 1]. As clearly illustrated in the figure, when the neural network is trained with regional cues, the neural network generates a more accurate activation map. Although the activation maps are not remarkably segmented enough to be segmented pixel by pixel and a small number of false positives appear in some cases, the activation maps derived by the present invention provide meaningful information about locations of findings that may be beneficially used by a clinician. The activation maps in which the guidance loss is absent highlight areas that are widely spread than the periphery of a lesion and frequently unrelated.

As described above, the present invention uses regional information about findings in fundus images for localization and classification over all of example embodiments and modification examples. Since effective labelling capable of collecting regional annotations about the findings is enabled, a neural network architecture capable of classifying findings with localization of lesions may be proposed. Accordingly, a medical workflow on a medical field in which a user, such as a medical staff, uses a medical image, such as a fundus image, may be enhanced.

One of ordinary skill in the art may easily understand that the methods and/or processes and operations described herein may be implemented using hardware components, software components, or a combination thereof based on the example embodiments.

The aforementioned functions and process stages may be automatically performed, or may be performed in response to the whole or some user commands. An activity (including an operation) automatically performed is performed in response to one or more instructions or device operation without direct initiation by the user of the activity.

The hardware components may include a general-purpose computer and/or exclusive computing apparatus or a specific computing apparatus or a special feature or component of the specific computing apparatus. The processes may be implemented using at least one microprocessor having an internal and/or external memory, a microcontroller, an embedded microcontroller, a programmable digital signal processor or other programmable devices. In addition, or, as an alternative, the processes may be implemented using an application specific integrated circuit (ASIC), a programmable gate array, a programmable array logic (PAL), or other devices configured to process electronic signals, or combinations thereof. Targets of technical solutions of the present invention or portions contributing to the arts may be configured in a form of program instructions performed by various computer components and stored in computer-readable recording media. The media may include, alone or in combination with program instructions, data files, data structures, and the like. The program instructions recorded in the media may be specially designed and configured for the example embodiments, or may be known to those skilled in the art of computer software. Examples of the media may include magnetic media such as hard disks, floppy disks, and magnetic tapes; optical media such as CD-ROM discs, DVDs, and Blu-ray; magneto-optical media such as floptical disks; and hardware devices that are specially configured to store and perform program instructions, such as ROM, RAM, flash memory, and the like. Examples of program instructions include both machine code, such as produced by a compiler and files containing structural programming languages such as C++ object-oriented programming language and high or low programming languages (assembly languages, hardware technical languages, database programming languages and techniques) to run not only on one of the aforementioned devices but also a processor, a processor architecture, or a heterogeneous combination of combinations of different hardware and software components, or a machine capable of executing program instructions. Accordingly, they may include a machine language code, a byte code, and a high language code executable using an interpreter and the like.

Therefore, according to an aspect of the present invention, the aforementioned methods and combinations thereof may be implemented by one or more computing apparatuses as an executable code that performs the respective operations. According to another aspect, the methods may be implemented by systems that perform the operations and may be distributed over a plurality of devices in various manners or all of the functions may be integrated into a single exclusive, stand-alone device, or different hardware. According to still another aspect, methods that perform operations associated with the aforementioned processes may include the aforementioned hardware and/or software. Such all of the sequences and combinations associated with the processes are to be included in the scope of the present invention.

For example, the described hardware devices may be to act as one or more software modules in order to perform processing according to the present invention, or vice versa. The hardware devices may include a processor, such as, for example, a micro processing unit (MPU), a central processing unit (CPU), a GPU, and a tensor processing unit (TPU), configured to be combined with a memory such as ROM/RAM configured to store program instructions and to execute the instructions stored in the memory, and may include a communicator capable of transmitting and receiving a signal with an external device. In addition, the hardware devices may include a keyboard, a mouse, and an external input device for receiving instructions created by developers.

While the present invention is described with reference to specific matters such as components, some example embodiments, and drawings, systems and processes of the accompanying drawings are not exclusive. Other systems, processes, and menus may be derived according to a principle of the present invention to achieve the same purpose. Although the present invention is described by referring to specific example embodiments, example embodiments illustrated herein and modification examples may be understood as having the purpose for the description only. The modifications related to a design of the present disclosure may be implemented by those skilled in the art without departing from the protective range of the present invention. As described herein, various systems, accompanying systems, agents, managers, and processes may be implemented using hardware components, software components, and/or combination thereof.

Therefore, the scope of the present invention is not defined by the example embodiments, but by the claims and their equivalents, and all variations within the scope of the claims and their equivalents are to be construed as being included in the present invention.

Such equally or equivalently modified example embodiments may include, for example, logically equivalent methods capable of achieving the same results as those acquired by implementing the method according to the present invention. Accordingly, the true meaning and the scope of the present invention are not limited to the aforementioned example embodiments and should be understood as a widest meaning allowable by law.

What is claimed is:

1. A method of classifying an image using a deep neural network, the method comprising:
    acquiring, by a computing apparatus, the image;
    generating, by a computing apparatus, classification information of the image based on the deep neural network; and
    providing, by a computing apparatus, the classification information to an external entity,
    wherein the classification information comprises a classification to which the image belongs and an activation map generated based on information of individual findings in the image related to the classification, and
    wherein the activation map includes visualization information indicating at least one location related to the individual findings in the image.

2. The method of claim 1, wherein the classification to which the image belongs is determined as at least one of a classification in which the image is non-interpretable, a classification in which the image is normal, and a classification in which the image is abnormal.

3. The method of claim 2, wherein, when the image belongs to the classification in which the image is abnormal, the activation map is generated based on locations of the individual findings.

4. The method of claim 2, wherein, when the image belongs to the classification in which the image is non-interpretable, an indication corresponding to "ungradable" is provided to the external entity.

5. The method of claim 2, wherein the classification information further comprises confidential level information regarding the classification in which the image is normal or the classification in which the image is abnormal.

6. The method of claim 1, further comprising:
    providing, by the computing apparatus, an interface of modifying and editing the classification information.

7. The method of claim 1, wherein the deep neural network is pretrained to decrease a value of a loss function calculated based on an input learning image, and the loss function is calculated based on a combination of a classification loss function that is calculated based on classification results of the deep neural network and a guidance loss function that is calculated based on the activation map.

8. The method of claim 7, wherein the guidance loss function is calculated based on an operation using a value of a first pixel comprised in a region mask provided as a label corresponding to the activation map and a value of a second pixel comprised in the activation map, and a location of the first pixel is determined as a location on the region mask corresponding to a location of the second pixel in the activation map.

9. The method of claim 8, wherein the guidance loss function is calculated based on a multiplication of a first function that is calculated based on the value of the first pixel and a second function that is calculated based on the value of the second pixel.

10. The method of claim 7, wherein the guidance loss function is represented as $$L_{guide}(A, M) = \frac{1}{kW_F H_F} \sum_{i=1}^{k} \sum_{l=1}^{W_F H_F} (1 - m_l^i) f(a_l^i + \epsilon)$$

where the k denotes a number of pieces of mini-batch data that at least a portion of learning data is extracted as mini-batch learning data, the $W_F$ is a natural number and denotes a width of an activation map about target findings, the $H_F$ is a natural number and denotes a height of the activation map, the $A=\{A^1, \ldots, A^k\}$ denotes the activation map about the target findings of the k mini-batch data where each of the $A^1, \ldots, A^k$ denotes a single element selected from a Descartes product of $W_F \times H_F$ dimension of a set (0, 1) having real numbers between 0 and 1 as elements, the $M=\{M^1, \ldots, M^k\}$ denotes a region mask about the target findings of the k mini-batch data where each of the $M^1, \ldots, M^k$ denotes a single element selected from a Descartes product of $W_F \times H_F$ dimension of a set {0, 1} having 0 and 1 as elements, the $m_l^i$ and the $a_l^i$, respectively, denote values of $l^{th}$ pixels of the $M^i$ and the $A^i$ for each natural number l greater than or equal to 1 and less than or equal to $W_F \times H_F$, the $A^i$ denotes a positive number introduced for a numerical stability, and the f denotes a function that is determined based on a log function.

11. The method of claim 10, wherein the $f(a_l^i,\epsilon)$ corresponds to one of log $(a_l^i+\epsilon)$ and $\log(\max(a_l^i+\epsilon))$.

12. The method of claim 1, wherein the deep neural network comprises a plurality of convolution layers, and comprises an output layer comprising a first output layer for outputting a guidance loss and a second output layer for outputting a classification loss as at least two output layers that follow a final 1×1 convolution layer.

13. The method of claim 12, wherein the first output layer calculates the classification through application of a sigmoid function after global average pooling (GAP) of the final 1×1 convolution layer, and the second output layer calculates the activation map through the sigmoid function application of the final 1×1 convolution layer.

14. The method of claim 1, wherein, before the image is input to the deep neural network, the computing apparatus performs preprocessing of cropping and resizing the image such that a fundus portion is positioned at a center of the image and the image is resized to have a size of between 256×256 and 1024×1024 and normalizing a pixel value of the image such that the pixel value of the image belongs to the range of 0 or more and 1 or less.

15. The method of claim 14, wherein, if the size of the image exceeds 512×512, a resolution of the image decreases for a size of 256×256 through a convolution of consecutive stride 2.

16. A non-transitory computer-readable record medium storing instructions that, when executed by a computing apparatus, cause the computing apparatus to perform the method of claim 1.

17. A computing apparatus for classifying an image using a deep neural network, the computing apparatus comprising:
a communicator configured to acquire the image; and
a processor configured to perform a process of generating classification information of the image based on the deep neural network and a process of providing the classification information to an external entity,
wherein the classification information comprises a classification to which the image belongs and an activation map generated based on information of individual findings in the image related to the classification, and
wherein the activation map includes visualization information indicating at least one location related to the individual findings in the image.

* * * * *